United States Patent [19]

Schulz et al.

[11] Patent Number: 5,043,488

[45] Date of Patent: Aug. 27, 1991

[54] PROCESS FOR PREPARING AN EXPLOSIVE AND THE PRODUCT THEREFROM

[75] Inventors: Johann G. Schulz; Engelina Porowski, both of Pittsburgh, Pa.

[73] Assignee: J. G. S. Research Company, Inc., Pittsburgh, Pa.

[21] Appl. No.: 491,966

[22] Filed: Mar. 12, 1990

[51] Int. Cl.$^5$ .......................................... C07C 201/00
[52] U.S. Cl. .................... 568/924; 568/926; 568/305; 162/29; 162/65; 162/139
[58] Field of Search ...................... 568/305, 924, 926; 162/29, 65, 139

[56] References Cited

U.S. PATENT DOCUMENTS

| | | | |
|---|---|---|---|
| Re. 30,459 | 12/1980 | Schweiger | 525/61 |
| 3,852,356 | 12/1974 | Weitz et al. | 568/924 X |
| 3,969,167 | 7/1976 | Johannes | 149/38 |
| 4,035,569 | 7/1977 | Schweiger | 536/32 |
| 4,496,783 | 1/1985 | Campbell et al. | 568/947 |
| 4,725,335 | 2/1988 | Samuelson | 162/81 |
| 4,750,973 | 6/1988 | Samuelson et al. | 162/65 |

OTHER PUBLICATIONS

Urbanski, "Chemistry and Technology of Explosives", vols. I, II and IV, The MacMillan Co., New York, 1964, pp. 82–83, 234–235 and 21–37, respectively.

Degering, "An Outline of Organic Nitrogen Compounds", University.Lithoprinters, Michigan, 1950, pp. 176–178, 700.

*Primary Examiner*—Robert L. Stoll
*Assistant Examiner*—Chhaya Sayala
*Attorney, Agent, or Firm*—Joseph J. Carducci

[57] ABSTRACT

A process for preparing an explosive comprising contacting a ketone with a compound capable of producing a product, or compound, containing nitro groups for a time sufficient to obtain a product having a high-energy content and the product resulting therefrom.

13 Claims, No Drawings

PROCESS FOR PREPARING AN EXPLOSIVE AND THE PRODUCT THEREFROM

BACKGROUND OF THE INVENTION

1. Field of the Invention

This invention relates to a process for preparing an explosive which comprises contacting a ketone with a compound capable of producing a product (or compound) containing nitro groups for a time sufficient to obtain a product having a high-energy content and the product resulting therefrom. 2. Description of the Prior Art Products having a high-energy content, that is, containing a substantial amount of nitrogen, such as nitrocellulose, trinitrotoluene, nitroglycerine, etc., are used extensively in commerce as explosives. Processes used to prepare such explosives can be expensive due to the conditions and reactants required therefor. Accordingly, it would be highly desirable to find a simple, relatively inexpensive means for producing a novel explosive using inexpensive materials and very simple operating procedures.

SUMMARY OF THE INVENTION

We have discovered a novel explosive containing a large amount of nitrogen and having a high-energy content that is prepared by bringing a ketone into contact with a product or compound containing nitro groups ($NO_2$) under relatively mild conditions of operation.

The ketone used can have from three to about twenty carbon atoms, preferably from three to about ten carbon atoms. Of these, we prefer to use acetone and methylethylketone, particularly acetone.

The only other component required in our novel process is a compound capable of producing a product containing nitro groups ($NO_2$), Note that "nitro groups" and "nitrogen dioxide" are identified as "$NO_2$" when such compound is subjected to the processing conditions defined below. Examples of such compounds are nitric acid; nitrous acid ($HNO_2$); nitrogen oxides, such as nitrogen oxide (NO), nitrogen dioxide ($NO_2$), nitrogen trioxide ($N_2O_3$), nitrogen tetraoxide ($N_2O_4$), nitrogen pentoxide ($N_2O_5$), etc; salts of nitric acid and nitrous acid, such as sodium nitrate, potassium nitrate, sodium nitrite, potassium nitrite, ammonium nitrite, etc. The nitric acid used is a 10 to 100 percent nitric acid, preferably a 40 to 70 percent nitric acid.

All that is required is that the ketone and the compound containing the nitro group be brought into intimate contact with each other. This is preferably done by adding the compound containing the nitro group to the ketone, generally over a period of time, in order better to control the progress of the reaction. The weight ratio of the ketone to the compound containing the nitro groups can vary over a wide range, for example, from about 1:100 to about 100:1, but we find best results are obtained within the range of about 1:1 to about 5:1.

Once the two components are brought into intimate contact with each, the resulting mixture is subjected to a temperature in the range of about 25° to about 250° C., but preferably in the range of about 50° to about 100° C. The start of reaction between the two is manifest by the generation of heat, causing a strong reflux, and the end thereof is apparent when no appreciable amount of heat is generated. In general, this period can vary from as little as about one-half hour to about eight hours, or more, but, in most cases, the reaction is completed within about two to about five hours. We have found that the process can be carried out adequately at atmospheric, or ambient, pressure, although pressures as high as about 200 pounds per square inch gauge, or even higher, can be used if desired. To reduce the induction period, small amounts of easily oxidizable organic substances such as alkyl aromatics (toluene, xylene, etc.), sawdust, etc., can be added to the reaction. Additionally, nitrogen oxides can also be used to reduce the induction period when other nitrogen-containing compounds defined above, are used to react with the ketone.

At the end of the reaction, the product can contain unreacted components and the desired novel explosive. To obtain, or recover, the desired novel explosive, the unreacted components can be removed from the reaction product using any known or convenient procedure. We have found that such removal can effectively be carried out by diluting the reaction product with water, for example, about 0.5 to about 10 volumes of water per volume of reaction product, and then subjecting the resulting aqueous mixture to vacuum distillation (for example, a pressure of about 500 to about 10 mm of Hg and a temperature of about 100° to about 30° C.) to remove unreacted ketone. The remaining product, with additional water, is further subjected to vacuum distillation (for example, a pressure of about 500 to about 10 mm of Hg and a temperature of about 30° to about 100° C.) to remove unreacted nitro-containing compounds therefrom. The product remaining behind is the novel explosive herein, is generally a straw-colored, viscous liquid. By "explosive" herein we mean a compound, or a mixture of compounds, which on heating, or as a result of mechanical impact or initiation by other energy-transfer mechanisms reacts spontaneously with evolution of large amounts of gaseous fragments.

The novel explosive is composed of water-soluble and water insoluble portions, of which we believe the water-insoluble portion has the greater explosive power. The mixture can be used as an explosive itself. If the water-insoluble portion is desired, the mixture can be diluted with water and the water-soluble portion can be removed therefrom using any conventional separator.

The novel explosive herein, before use, can be maintained in a stabilized condition in any suitable manner, for example, by diluting the same with methanol. When the novel explosive is to be used, methanol can be removed therefrom using conventional means, for example, at vacuum distillation at low temperatures, for example a pressure of about 10 to about 100 mm of Hg and a temperature of about 2° to about 50° C.

DESCRIPTION OF PREFERRED EMBODIMENTS

A number of runs was carried out using various nitrocontaining compounds and ketones and wherein recovery of the novel explosive from the reaction product was effected using the means described above, namely, addition of water and subsequent vacuum distillation at low temperatures. The results obtained are tabulated below:

TABLE I

| Example No. | 1 | 2 | 3 |
|---|---|---|---|
| Reaction time, hr | 2.5 | 5.0 | 6.0 |

TABLE I-continued

| Example No. | 1 | 2 | 3 |
|---|---|---|---|
| Temperature, °C. | 55 | 35 | 25 |
| Acetone, ml (g) | 750(589) | 750(589) | 750(589) |
| HNO₃ (70%), g | 214 | 214 | 214 |
| Acetone/HNO₃, weight ratio | 2.75 | 2.75 | 2.75 |
| Total explosive obtained, g | 118.0 | 25.2 | 3.2 |
| HNO₃ consumed, wt. % | 66 | 23 | 3 |

Table I shows the temperature of the reaction is important is important in that best results were obtained at about 55° C.-70° C. Elemental analysis of the explosive obtained in example No. 1 is set forth below in Table II.

TABLE II

|  | Weight Percent |
|---|---|
| Carbon | 37.08 |
| Hydrogen | 6.54 |
| Nitrogen | 17.20 |
| Oxygen | 38.48 |

TABLE III

| Example No. | 4 | 5 | 6 | 7 |
|---|---|---|---|---|
| Reaction time, hr | 2.0 | 2.5 | 2.5 | 2.5 |
| Temperature °C. | 55 | 55 | 55 | 55 |
| Acetone, ml (g) | 250(196) | 250(196) | 250(196) | 250(196) |
| HNO₃, (70%), g | 214 | 214 | 214 | 214 |
| Acetone/HNO₃, weight ratio | 0.9 | 0.9 | 0.9 | 0.9 |
| H₂O, g | 0 | 20 | 40 | 120 |
| Total explosive obtained, g | 73.7 | 72.4 | 73.5 | 67.0 |
| HNO₃ consumed, wt % | 54 | 54 | 54 | 54 |

The data in Table III appears to indicate that the dilution of the nitric acid with water has little, if any, effect on the product yields.

TABLE IV

| Example No. | 8 | 9 | 10 | 11 |
|---|---|---|---|---|
| Reaction time, hr. | 2.7 | 2.5 | 2.5 | 2.5 |
| Temperature, °C. | 55 | 55 | 55 | 55 |
| Acetone, g | 198 | 396 | 589 | 789 |
| HNO₃ (70%), g | 214 | 214 | 214 | 214 |
| Acetone/HNO₃, weight ratio | 0.93 | 1.85 | 2.75 | 3.7 |
| Total explosive obtained, g | 73.7 | 106.1 | 118.0 | 117.0 |
| HNO₃ consumed, wt % | 54 | 62 | 66 | 65 |

The data in Table IV shows that the acetone to nitric acid weight ratio has a pronounced effect on yields. Thus, yields of product increase with rising ratios of acetone to nitric acid up to a point,, after which no further benefit is realized.

EXAMPLE NO. 12

A total of 214 grams of 70 weight percent aqueous nitric acid were gradually added to 433 grams of acetone in a glass flask immersed in a water bath kept at 60° to 70° C. After 130 grams of the nitric acid had been added over a period of one hour, the reaction started, manifest by strong acetone reflux and a change of color from colorless to a light yellow. The remainder of the nitric acid was then added in two equal portions in five minute intervals and the reaction was allowed to proceed for an additional 20 minutes. 98.6 grams of a yellow, liquid product was recovered, using the recovery procedures described above.

EXAMPLE NO. 13

214 grams of 70 weight percent aqueous nitric acid were gradually introduced into 443 grams of acetone in a flask in a water bath kept at 60° to 70° C. Prior to the addition, one gram of sawdust had been added to the acetone. In this run 120 grams of the total nitric acid used were introduced over the first 25 minutes, after which the reaction started. The remainder of the nitric acid was added over the next 15 minutes, maintaining a vigorous reaction for half an hour. 103.5 grams of a light yellow, liquid product were recovered, using the recovery procedure described above.

EXAMPLE 14

107 grams of 70 weight percent aqueous nitric acid were added in a single portion to 394 grams of acetone in a flask immersed in a water bath kept at 60° to 70° C. Small amounts of gaseous nitric oxides (NO and NO₂) were then introduced into the reaction mixture, whereupon the reaction started immediately. The remainder of the nitric acid was then added to the boiling mixture over a period of one hour, followed by a holding time of one hour. 105.1 grams of a light yellow product were recovered following the recovery procedures described above.

EXAMPLE 15

20 grams of 70 weight percent aqueous nitric acid, 120 grams of methylethylketone and two grams of sawdust were placed into a flask immersed in a water bath kept at 60° to 70° C. After the reaction failed to commence within a half hour, a subsequent 30 grams of nitric acid were added in three equal portions. The color of the reaction mixture changed from colorless to yellow and finally to bright green, accompanied by evolutions of heat, causing a strong reflux. The reaction subsided within the next half hour, while the green color disappeared. Additions of the remaining 14 grams of nitric acid produced the green color again. The reaction was discontinued when refluxing subsided. 30 grams of a dark yellow liquid product were recovered using the recovery procedure described above. Elemental analyses of the explosive obtained in this Example No. 15 is set forth below in Table V.

TABLE V

|  | Weight Percent |
|---|---|
| Carbon | 44.29 |
| Hydrogen | 5.90 |
| Nitrogen | 14.10 |
| Oxygen | 35.71 |

EXAMPLE NO. 16

One gram of the novel product obtained in Example No. 1 was placed on a small metal disk disposed on a hot plate to which a thermocouple was attached. The temperature of the material on the disk was gradually increased from its ambient state. When the temperature reached 40° C., the material decomposed violently with copious evolution of smoke and flame indicating it to be an excellent explosive.

It should be noted that the recovered material of Example No. 1, used in Example No. 16, had a nitrogen content of 17.20 weight percent and that of Example No. 15 had a nitrogen content of 14.10 weight percent. In our work, we have obtained explosives having as much as 18.5 weight percent nitrogen. This can be compared with nitrocellulose having from 10.75 to 13.40 weight percent nitrogen (Ullmann's Encyklopadie der Technischen Chemie, Verlag Chemie Weinheim, New York, N.Y., 4th Edition, Volume 17, page 345), trinitrotoluene having 13 weight percent nitrogen and nitroglycerine having 19 weight percent nitrogen.

Obviously, many modifications and variations of the invention, as hereinabove set forth, can be made without departing from the spirit and scope thereof, and therefore only such limitations should be imposed as are indicated in the appended claims.

We claim:

1. A process for preparing an explosive which comprises contacting a ketone with aqueous nitric acid for about one-half to about eight hours to obtain an explosive.

2. The process of claim 1 wherein said ketone has from three to about twenty carbon atoms.

3. The process of claim 1 wherein said ketone has from three to about twenty carbon atoms.

4. The process of claim 1 wherein said ketone is acetone.

5. The process of claim 1 wherein said ketone is methylethylketone.

6. The process of claim 1 wherein the weight ratio of ketone to said nitric acid is from about 1:100 to about 100:1.

7. The process of claim 1 wherein the weight ratio of ketone to said nitric acid is from about 1:1 to about 5:1.

8. The process of claim 1 wherein said process is carried out at a temperature in the range of about 25° to about 250° C.

9. The process of claim 1 wherein said process is carried out at a temperature in the range of about 50° to about 100° C.

10. The process of claim 1 wherein sawdust is also present during the reaction sufficient to reduce the induction period.

11. The process of claim 1 wherein a nitrogen oxide is also present during the reaction sufficient to reduce the induction period.

12. The explosive resulting from the process of claim 1.

13. The process of claim 1 wherein said aqueous nitric acid is a 10 to 70 weight percent nitric acid.

* * * * *